United States Patent [19]

Mross et al.

[11] Patent Number: 4,529,714
[45] Date of Patent: Jul. 16, 1985

[54] PROCESS FOR REGENERATING SILVER-CONTAINING CARRIER CATALYSTS FOR THE PREPARATION OF ETHYLENE OXIDE

[75] Inventors: Wolf D. Mross, Frankenthal; Matthias Schwarzmann, Limburgerhof; Juergen Plueckhan, Frankenthal; Juergen Dehler, Neuhofen, all of Fed. Rep. of Germany

[73] Assignee: BASF Aktiengesellschaft, Ludwigshafen, Fed. Rep. of Germany

[21] Appl. No.: 579,085

[22] Filed: Feb. 10, 1984

[30] Foreign Application Priority Data

Feb. 19, 1983 [DE] Fed. Rep. of Germany ....... 3305805

[51] Int. Cl.$^3$ ................... B01J 23/96; C07D 301/10; C07D 303/04
[52] U.S. Cl. ........................................ 502/25; 502/26; 502/29; 502/33; 549/534
[58] Field of Search ....................... 502/25, 26, 29, 33, 502/347, 348

[56] References Cited

U.S. PATENT DOCUMENTS

| | | | |
|---|---|---|---|
| 4,224,194 | 9/1980 | Cavitt | 502/347 |
| 4,229,321 | 10/1980 | Cavitt | 502/347 |
| 4,278,562 | 7/1981 | Mross et al. | 502/348 |
| 4,324,699 | 4/1982 | Mross et al. | 502/347 |
| 4,361,504 | 11/1982 | Solomon et al. | 502/348 |

Primary Examiner—P. E. Konopka
Attorney, Agent, or Firm—David L. Hedden

[57] ABSTRACT

The subject invention relates to a process for regenerating silver-containing carrier catalysts used in the preparation of ethylene oxide which comprises treating a deactivated catalyst with a solution comprising a potassium, rubidium, or cesium compound and a reducing agent. The subject process provides improved catalyst regeneration.

17 Claims, No Drawings

PROCESS FOR REGENERATING SILVER-CONTAINING CARRIER CATALYSTS FOR THE PREPARATION OF ETHYLENE OXIDE

BACKGROUND OF THE INVENTION

1. Field of the Invention

This invention relates to an improved process for regenerating carrier catalysts used in the preparation of ethylene oxide. The carrier catalysts primarily consist of silver and, in some cases, alkali metal compounds, in particular cesium, as promoters.

2. Description of the Prior Art

Carrier catalysts as well as their preparation are generally known, for example, in published document EP-B1 00 14 457 (assigned to BASF AG and hereinafter referred to as EP-B1). In and of themselves carrier catalysts are very suitable for the preparation of ethylene oxide from ethylene and oxygen. However, since their effectiveness diminishes the longer they are in service, efforts have been made to find ways to regenerate them without having to remove them from the ethylene oxide reactor.

Thus, various treatment processes have been developed in which the deactivated catalyst is treated with compounds of heavy alkali metals, in particular with cesium compounds. In published documents DE-A 25 19 599 and 26 11 856 (Hoechst AG) the deactivated catalyst is treated with alcohol solutions of the alkali metal compounds; in published documents DE-A 26 49 359 (Hoechst AG) this treatment is performed in at least two steps, whereby the ethylene oxide production is continued between these steps; in published document DE-A 27 40 480 (Hoechst AG) the catalyst is washed in an inert liquid prior to treatment with the alkali metal; in DE-A 29 38 245 (Hoechst AG) the washing fluid contains ammonia or aliphatic amines; and in EP-B1, cited previously, the catalyst is treated in the presence of a surfactant and, preferably, a complexing agent such as 2-aminobutane.

EP-B1, in addition to disclosing the regeneration of the catalyst, also teaches its preparation and thus also the initial treatment of the fresh silver catalyst with the compounds of the heavy alkali metals and a reducing agent such as hydrazine, optionally with a surfactant as well as a complexing agent for silver (I) ions. However, EP-B1 does not teach the use of a reducing agent in the regeneration of the catalyst.

SUMMARY OF THE INVENTION

The subject invention relates to a process for regenerating a silver-containing carrier catalyst used in the preparation of ethylene oxide which comprises treating the deactivated catalyst with a solution comprising a potassium, rubidium, or cesium compound and a reducing agent.

It is preferred to use compounds which form complexes with monovalent silver ions and/or surfactants. It is also preferred to use hydrazine as the reducing agent.

The subject process provides improved catalyst regeneration.

DESCRIPTION OF THE PREFERRED EMBODIMENTS

The catalysts to be regenerated, identified below as "ethylene oxide catalysts," are generally known, for example, as cited in EP-B1 00 14 457. Their carrier material comprises, for example, silicates, quartz, silicon-carbide, graphite or, most preferably, α-aluminum oxide, and their active layer is comprised of silver. In addition, this layer can be treated with ions of the light alkali metals, lithium and sodium, as well as with ions of the heavy alkali metals potassium, rubidium, and, in particular, cesium.

Such catalysts can have a composition similar to the following (in weight percent):

| | | |
|---|---|---|
| Carrier material (in particular α-Al$_2$O$_3$) | 88–98, | preferably 88–94% |
| Silver | 2–12, | preferably 6–12% |
| Li$^+$ + Na$^+$ | 0–0.03, | preferably 0.005–0.025% |
| Li$^+$ | 0–0.025, | preferably 0.004–0.015% |
| Na$^+$ | 0–0.035, | preferably 0.004–0.025% |
| Atomic ratio (rounded off) Ag: (Li$^+$ + Na$^+$) = 5:1 to ∞, | | preferably 15:1–150:1 |
| Heavy Alkali Metal in particular Cs$^+$ | 0–0.025, | preferably 0.005–0.025% |
| Atomic ratio (rounded off) Ag: (K$^+$ + Rb$^+$ + Cs$^+$) 10:1 to ∞, | | preferably 200:1–5000:1 |

The treatment solution used to regenerate these catalysts contains a heavy alkali metal, in particular, cesium, regardless of whether or not the original catalyst contains any alkali metals as promoters. Since the presence of the alkali metal cations is usually found in fresh ethylene oxide catalysts of the type described, though, as a rule the regeneration generally involves catalysts which originally contained such promoters. In this case the regeneration takes place because the compounds of the heavy alkali metals are again replaced after having been partially or completely transformed into a catalytically inactive form during the course of catalyst service.

The amount and concentration of the treatment solution necessary to regenerate the catalysts varies depending on the liquid up-take and the type of solvent. However, these variables can be determined by a few preliminary tests. In general, the amount is 100 ml to 500 ml per kilogram of catalyst and its heavy alkali metal cation content is approximately 0.005 to 0.15, preferably 0.01 to 0.1 weight percent based upon the weight of the catalyst.

Preferably, C$_1$–C$_3$ alkanols are used as solvents. Primarily hydroxides and nitrates are used as the heavy alkali metal compounds, but carbonates and the salts of carboxylic acids can also be used.

According to this invention, the treatment solutions further contain active amounts of a reducing agent. These active amounts cannot be precisely cited for all cases and, therefore, must be determined through several preliminary tests. In general, they are not less than 0.05 g per kilogram catalyst and they are preferably between 0.5 and 5 g per kilogram catalyst. Larger quantities do not produce further advantages; on the other hand, observations so far also indicate that they do not do any harm.

In principle, any reducing agent can be used, of course, excepting those containing catalyst poisons such as halogen or sulfur. Typical examples of reducing agents are: hydroquinone, p-aminophenol, p-diaminobenzene, p-hydroxy-N-methylaniline and, preferably, hydrazine.

In addition to the reducing agents, the simultaneous use of compounds in the treatment solution which form complexes with Ag$^+$(I) ions is recommended. Such complexing agents are, for example, diketones such as diacetyl and acetylacetone, acetates, polyethers having the structural unit —CH$_2$—CH$_2$—O—, in particular the so-called crown ethers. Typical nitrogen-containing complexing agents are acetonitrile, mono-, di-, and trialkyl- and trialkanolamines having a total of up to 6 carbon atoms, ethylenediamine and piperazine, in particular, ammonia, nitriles, and amines, among these amines preferably aliphatic and cycloaliphatic amines. 2-aminobutane has proved to be particularly suitable.

These complexing agents are best used in the treatment solutions at concentrations of from 0.1 to 30 weight percent, preferably from 0.1 to 10 weight percent.

In addition, the use of surfactants is recommended in regenerating the catalysts. Theoretically, all sulfur- and halogen-free wetting agents are suitable; however, nonionic surfactants are preferred. Typical nonionic surfactants are generally polyglycol ethers (ethoxylation products) of aliphatic, cycloaliphatic, and alkylaromatic alcohols such as fatty acid esters and fatty acid amides. Examples are the standard commercial surfactants, maleic acid ethanolamine, the monostearate of triethanolamine, the reaction product of nonylphenol and 14 moles ethylene oxide, and the reaction product of oleylamine and 12 moles ethylene oxide.

The surfactants develop their desired effectiveness at very low concentrations, however, they are generally used at concentrations from 0.1 to 10 weight percent, preferably 0.1 to 5 weight percent, in the treatment solution.

In the technically simplest method of catalyst regeneration, the treatment solution is passed by the fixed catalyst and the excess solvent is blown off with, for example, nitrogen. The catalyst is then dried and gradually heated under nitrogen to from 150° C. to 300° C. After having been treated in this way, the catalyst is again ready for service.

The use of the regenerated catalysts to prepare ethylene oxide from ethylene and oxygen in the gaseous phase then takes place under conventional conditions, i.e., at an ethylene/O$_2$ molar ratio of from 0.5:1 to 5:1, at a pressure from 1 bar to 50 bars, and at a temperature from 150° C. to 350° C., in some cases with inert gases and inhibitors also being used. Those skilled in the art are aware of the specific equipment and procedures used.

EXAMPLE

An ethylene oxide catalyst was regenerated after approximately four years' service. The catalyst originally had the following composition:

| | | |
|---|---|---|
| —Al$_2$O$_3$ | 92.5 | weight percent |
| Silver | 7.5 | weight percent |
| Li$^+$ | 0.018 | weight percent |
| Cs$^+$ | 0.0145 | weight percent. |

During the course of this four-year service, the catalytic activity diminished from an initial 81.5 percent to 76.7 percent.

This catalyst was treated in a methanol solution in a test apparatus used for the preparation of ethylene oxide. Depending on the test, the methanol solution contained from 0.25 to 20 weight percent CsOH in addition to the additives listed in the table. After treatment, the catalyst was dried in a stream of nitrogen and then heated to 200° C. for approximately 10 minutes.

A gas mixture comprising 8 volume percent oxygen, 30 volume percent ethylene, 1 ppm vinyl chloride, and 62 percent nitrogen was passed through the various resulting catalyst samples (particle size 0.5 to 0.6 mm, amount of catalyst 5 g) at 15 bar and T° C. The temperature T, which is an index for the activity of the catalyst A, was adjusted such that an oxygen conversion of 50 percent was obtained in each test. From this, it was possible to determine the selectivities S for ethylene oxide.

The test data and the results from these tests are shown in the Table.

As the Table shows, the regeneration effect achieved with the reducing agent is significantly better than in the tests with other auxiliaries. However, these auxiliaries do intensify the effect of the reducing agent when used together with it.

TABLE

| Test No. | Cs$^+$ Content in Catalyst Weight Percent | Reducing Agent | Concentration of Regenerating Additives (weight %) Complexing Agents | Surfactants | S % | A °C. |
|---|---|---|---|---|---|---|
| Comparison Tests | | | | | | |
| A. Without Regeneration | | | | | | |
| 1. original catalyst at beginning | 0.0145 | — | — | — | 81.5 | 218 |
| 2. original catalyst after four years | 0.0140 | — | — | — | 76.7 | 247 |
| B. After regeneration of catalyst with auxiliaries but without reducing agent | | | | | | |
| 3. | 0.0215 | — | 2-aminobutane; 4.0 | — | 77.2 | 249 |
| 4. | 0.0240 | — | " | — | 77.4 | 251 |
| 5. | 0.0250 | — | " | — | 77.7 | 254 |
| 6. | 0.0215 | — | ethanolamine; 4.0 | Oleic acid | 77.1 | 250 |
| Examples (after regeneration with reducing agent) | | | | | | |
| 7. | 0.0215 | Hydrazine; 1.0 | — | — | 77.8 | 248 |
| 8. | 0.0240 | " | — | — | 78.0 | 250 |
| 9. | 0.0250 | " | — | — | 78.3 | 250 |
| 10. | 0.0215 | " | 2-aminobutane; 4.0 | — | 79.8 | 247 |

TABLE-continued

| Test No. | Cs+ Content in Catalyst Weight Percent | Reducing Agent | Concentration of Regenerating Additives (weight %) | | S % | A °C. |
|---|---|---|---|---|---|---|
| | | | Complexing Agents | Surfactants | | |
| 11. | 0.0240 | ″ | ″ | — | 79.8 | 247 |
| 12. | 0.0250 | ″ | ″ | — | 79.9 | 248 |
| 13. | 0.0215 | ″ | — | Oleic acid | 79.0 | 251 |
| 14. | 0.0215 | p-aminophenol; 1.0 | ethanolamine; 4.0 2-aminobutane; 4.0 | — | 78.8 | 252 |

The embodiments of the invention in which an exclusive privilege or property is claimed are defined as follows:

1. A process for regenerating silver-containing carrier catalysts useful in the preparation of ethylene oxide, which comprises treating the deactivated catalyst with a solution comprising an effective amount of a potassium, rubidium or cesium compound and an effective amount of a reducing agent which does not contain any significant amount of halogen or sulfur.

2. The process of claim 1 wherein the regeneration is carried out with a cesium compound.

3. The process of claim 1 wherein hydrazine is used as the reducing agent.

4. The process of claim 2 wherein hydrazine is used as the reducing agent.

5. The process of claim 3 wherein a compound which forms complexes with Ag+(I) ions is used in addition as the reducing agent.

6. The process of claim 4 wherein a compound which forms complexes with Ag+(I) ions is used in addition as the reducing agent.

7. The process of claim 5 wherein the complexing agent is 2-aminobutane.

8. The process of claim 6 wherein the complexing agent is 2-aminobutane.

9. The process of claim 1 wherein a surfactant is used in addition to the reducing agent.

10. The process of claim 2 wherein a surfactant is used in addition to the reducing agent.

11. The process of claim 3 wherein a surfactant is used in addition to the reducing agent.

12. The process of claim 4 wherein a surfactant is used in addition to the reducing agent.

13. The process of claim 5 wherein a surfactant is used in addition to the reducing agent.

14. The process of claim 6 wherein a surfactant is used in addition to the reducing agent.

15. The process of claim 7 wherein a surfactant is used in addition to the reducing agent.

16. The process of claim 8 wherein a surfactant is used in addition to the reducing agent.

17. The process of claim 1 wherein the amount of potassium, rubidium, or cesium cation in the solution is from 0.005 to 0.15 weight percent based upon the weight of the catalyst, and the amount of reducing agent is from 0.05 grams per kilogram catalyst to 5 grams per kilogram catalyst.

* * * * *